(12) United States Patent
Maas et al.

(10) Patent No.: US 7,388,116 B2
(45) Date of Patent: Jun. 17, 2008

(54) HYDROGENATION OF METHYLOLALKANALS

(75) Inventors: Steffen Maas, Bubenheim (DE);
Thorsten Johann, Ludwigshafen (DE);
Michael Koch, Mannheim (DE);
Tilman Sirch, Schifferstadt (DE);
Stephan Schlitter, Limburgerhof (DE);
Stefan Rittinger, Mannheim (DE);
Michael Steiniger, Neustadt (DE);
Todd C Spengeman, Missouri City, TX (US)

(73) Assignee: BASF Aktiengesellschaft, Ludwigshafen (DE)

( * ) Notice: Subject to any disclaimer, the term of this patent is extended or adjusted under 35 U.S.C. 154(b) by 53 days.

(21) Appl. No.: 11/447,020

(22) Filed: Jun. 6, 2006

(65) Prior Publication Data

US 2007/0282135 A1 Dec. 6, 2007

(51) Int. Cl.
*C07C 27/04* (2006.01)
(52) U.S. Cl. ............... 568/799; 568/862; 568/892
(58) Field of Classification Search ............... None
See application file for complete search history.

(56) References Cited

U.S. PATENT DOCUMENTS

| | | | |
|---|---|---|---|
| 3,808,280 A | 4/1974 | Merger et al. | |
| 4,288,640 A | 9/1981 | Schuster et al. | |
| 4,386,018 A | 5/1983 | Merger et al. | |
| 6,018,074 A | 1/2000 | Kratz et al. | |
| 6,187,971 B1 | 2/2001 | Kratz et al. | |
| 6,201,160 B1 | 3/2001 | Brudermueller et al. | |
| 6,255,541 B1 | 7/2001 | Paatero et al. | |
| 2003/0009062 A1 | 1/2003 | Dobert et al. | |
| 2004/0082821 A1 | 4/2004 | Koch et al. | |

FOREIGN PATENT DOCUMENTS

| | | |
|---|---|---|
| DE | 1 941 633 | 3/1971 |
| DE | 1 957 591 | 5/1971 |
| DE | 2 040 501 | 2/1972 |
| DE | 25 07 461 | 9/1976 |
| DE | 199 63 441 A1 | 7/2001 |
| EP | 0 044 444 A1 | 1/1982 |
| GB | 1 362 071 | 7/1974 |
| GB | 1 535 826 | 12/1978 |
| WO | WO 95/32171 | 11/1995 |
| WO | WO 97/17313 | 5/1997 |
| WO | WO 98/28253 | 7/1998 |
| WO | WO 98/29374 | 7/1998 |
| WO | WO 01/51438 A1 | 7/2001 |
| WO | WO 02/085825 A2 | 10/2002 |

OTHER PUBLICATIONS

Carroll W. Griffin, "The Adsorption of Hydrogen And Ethylene on A Copper Catalyst Poisoned With Carbon Monoxide", JACS, vol. 49, Sep. 2, 1927, pp. 2136-2145.

*Primary Examiner*—Sikarl A Witherspoon
(74) *Attorney, Agent, or Firm*—Oblon, Spivak, McClelland, Maier & Neustadt, P.C.

(57) ABSTRACT

Process for the catalytic hydrogenation of methylolalkanals of the general formula

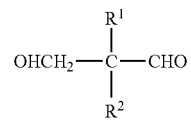

where $R^1$ and $R^2$ are each, independently of one another, a further methylol group or an alkyl group having from 1 to 22 carbon atoms or an aryl or aralkyl group having from 6 to 33 carbon atoms, in the liquid phase by means of hydrogen over a hydrogenation catalyst, wherein hydrogen is used in a molar ratio to methylolalkanal of greater than 1.

18 Claims, No Drawings

HYDROGENATION OF METHYLOLALKANALS

The invention relates to a process for preparing polyhydric alcohols by catalytic hydrogenation of methylolalkanals in the liquid phase over a hydrogenation catalyst at a superstoichiometric hydrogen/methylolalkanal ratio.

The catalytic hydrogenation of carbonyl compounds such as aldehydes for preparing simple and functionalized alcohols occupies an important position in production lines of the basic chemicals industry. This is particularly true of the hydrogenation of aldehydes which can be obtained via the oxo process or aldol reaction.

Methylolalkanals can be obtained by aldol reaction of alkanals with excess formaldehyde in the presence of stoichiometric amounts of base. It is known from WO 01/51438 that inorganic hydroxides such as sodium hydroxide or calcium hydroxide can be used as base. WO 98/28253 and DE-A 1 957 591 describe amines as basic catalysts for aldolization and WO 98/29374 describes basic ion exchangers. In these processes, the methylolalkanal is obtained as a 20-80% strength by weight aqueous solution. The pH of the solution is only from 3.5 to 6.0 since the basic catalyst for the aldolization also catalyzes the Cannizzaro reaction of the formaldehyde to form formic acid which in turn at least partly neutralizes the base.

If polyhydric alcohols such as pentaerythritol, neopentyl glycol or trimethylolpropane are to be prepared from aqueous methylolalkanal solutions, the solutions have to be hydrogenated.

This hydrogenation is generally carried out at temperatures above 80° C. Redissociation of the methylol group to the free aldehyde, the Cannizzaro reaction of formaldehyde to form formic acid and also ether, ester and acetal formation are observed in the hydrogenation reactor. These secondary reactions lead to low hydrogenation selectivities and to low yields of the polyhydric alcohol.

In addition, many hydrogenation catalysts are not stable under these conditions. Catalysts based on the oxides of aluminum and silicon as are known from EP-A 44 444 and WO 95/32171, in particular, lose activity in the presence of these aqueous methylolalkanal solutions under hydrogenation conditions, which has been found to lead to a significantly reduced conversion over a period of a few months.

Formic acid which has been formed in the aldolization as by-product from formaldehyde via a Cannizzaro reaction is decomposed to $CO_2$ and $H_2$ or to CO and $H_2O$ during the course of the industrial hydrogenation. CO and $CO_2$ can be detected in the offgas from the hydrogenation and have an adverse effect on the hydrogenation activity of the catalyst. Deliberate addition of CO or $CO_2$ to the hydrogen leads to a significant decrease in the hydrogenation activity of the copper catalyst, even when the $H_2$ partial pressure, the absolute amount of $H_2$ and the pH in the hydrogenation reactor have been kept constant.

CO and $CO_2$ have long been known as catalyst poisons for copper and nickel catalysts, for example from C. W. Griffin, JACS (1927) 49, 2136-2145, and many methods of regenerating catalysts which have been deactivated by CO and $CO_2$ have been developed.

Thus, for example, DE-A 199 63 441 describes a method of regenerating a copper catalyst by "burning off". Here, oxygen is passed over the active catalyst at elevated temperature. Under these conditions, organic deposits are oxidized to $CO_2$ and the active copper is oxidized to copper oxide.

These regenerations are complicated and generally require stoppage of the industrial plant. It is therefore more economical to delay the regeneration for as long as possible and to choose operating conditions in the hydrogenation which enable the catalyst to achieve a long operating life.

It was therefore an object of the invention to provide a process for preparing polyhydric alcohols by catalytic hydrogenation of methylolalkanals, in which polyhydric alcohols can be made available with good conversions and yields and also long operating lives of the catalyst.

This object is achieved by a process for preparing polyhydric alcohols by catalytic hydrogenation of methylolalkanals of the general formula

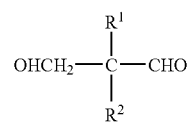

where $R^1$ and $R^2$ are each, independently of one another, a further methylol group or an alkyl group having from 1 to 22 carbon atoms or an aryl or aralkyl group having from 6 to 33 carbon atoms, in the liquid phase by means of hydrogen over a hydrogenation catalyst, wherein hydrogen is used in a molar ratio to methyloialkanal of greater than 1.

According to the invention, it has been recognized that at superstoichiometric hydrogen/starting material molar ratios (hydrogen/methylolalkanal molar ratios) the amount of offgas from the hydrogenation is increased and the concentration of CO or $CO_2$ in the hydrogenation reactor can be set. The deactivating effect of CO or $CO_2$ can be significantly reduced by the process of the invention. The hydrogenation catalyst can be kept at a high activity level, i.e. high conversions and yields are achieved at long catalyst operating lives.

The hydrogen/methylolalkanal molar ratio is preferably set to a value of from 5 to 1, particularly preferably to a value of from 2.5 to 1.1.

To set the hydrogen/methylolalkanal molar ratios used according to the invention, either a fixed ratio of hydrogen to hydrogenation feed is set by means of the process control system or the amount of hydrogen is controlled so that less than 4000 ppm of CO, preferably less than 1000 ppm of CO, are comprised in the reaction offgas. The determination of CO can be carried out either continuously via an on-line measurement in the offgas stream or discontinuously by means of gas-chromatographic analysis in a manner known per se.

The amount of hydrogen which is not consumed chemically by hydrogenation leaves the reactor as offgas and can, for example, be used in combustion for energy generation. It is also possible to separate the offgas from the hydrogenation into its constituents and recover the hydrogen as starting material. A third form of utilization is use of the hydrogen in a process in which the secondary constituents originating from the hydrogenation do not interfere.

For the purposes of the present patent application, hydrogenation feed is an aqueous solution comprising a methylolalkanal of the general formula I, in particular an aqueous solution comprising from 20 to 80% by weight of methylolalkanal. Such a hydrogenation feed is preferably prepared as described in WO 98/28253 or DE-A 1 957 591 by reaction of aldehydes with formaldehyde.

In this reaction, the aldehyde is reacted with from 1 to 8 times its amount of formaldehyde in the presence of a tertiary amine (aldolization) and the reaction mixture obtained in this way is separated into two solutions, with one solution comprising the abovementioned methylolalkanal and the other solution comprising unreacted starting material. This latter solution is recirculated to the reaction. The separation is carried out by distillation or simple separation of the aqueous phase from the organic phase. The aqueous solution comprising the methylolalkanal can be used as hydrogenation feed in the process of the invention.

However, it is also possible to produce the aqueous methylolalkanal solution used as hydrogenation feed by other processes of the prior art, for example by the processes known from WO 01/51438, WO 97/17313 and WO 98/29374.

In a preferred variant of the process of the invention, an aqueous methylolalkanal solution which is particularly low in formaldehyde or is free of formaldehyde is used as hydrogenation feed. In a low-formaldehyde methylolalkanal solution, the formaldehyde content is less than 5% by weight. The separation of formaldehyde from the aldolization product mixture which has been obtained, for example, as described in WO 98/28253 can be effected by methods known from the prior art, for example by distillation.

The methylolalkanal of the general formula I is preferably a dimethylolalkanal, pentaerythrose or hydroxypivalaldehyde.

The hydrogenation feed can be mixed upstream of the inlet into the hydrogenation reactor with tertiary amine, inorganic base or inorganic or organic acid until the hydrogenation output taken off downsteam of the reactor outlet has a pH of from 7.0 to 9.0, for the preparation of neopentyl glycol preferably a pH of from 8.0 to 9.0, for the preparation of trimethylolpropane a pH of from 6.0 to 8.0. It is also possible to feed the hydrogenation feed and the tertiary amine, the inorganic base or the inorganic or organic acid separately into the reactor and mix them there.

As suitable tertiary amines, mention may be made by way of example of the amines indicated in DE-A 25 07 461. Preferred tertiary amines are tri-n-$C_1$-$C_4$-alkylamines, particularly preferably trimethylamine, triethylamine, tri-n-propylamine and tri-n-butylamine. In general, up to 10% by weight (based on the hydrogenation feed) of the tertiary amine are used in the process of the invention to control the pH. The amine can be used as pure substance or as aqueous solution.

It is particularly advantageous to use amines for setting the pH since they form thermally decomposable salts with formic acid, and these can be redissociated after the hydrogenation. This enables formation of salts to be avoided and the tertiary amine to be recirculated to the process.

It is particularly advantageous to use the same tertiary amine in the aldolization process to form the methylolalkanal, viz. the condensation of a higher aldehyde and formaldehyde, and in the hydrogenation.

As inorganic or organic acids, it is possible, according to the invention, to use mineral acids such as hydrochloric acid, sulfuric acid or phosphoric acid or organic acids such as citric acid, acetic acid or ethylhexanoic acid. Preference is given to using acetic acid. In general, from 0 to 3% by weight (based on the hydrogenation feed) of a 10% strength aqueous solution of the acid is added to control the pH.

The pH is measured using known techniques, for example by means of a glass electrode and a pH meter.

Catalysts which can be used for the purposes of the invention are catalysts which are suitable for hydrogenations and preferably comprise at least one metal of transition groups 8 to 12 of the Periodic Table of the Elements, e.g. Fe, Ru, Os, Co, Rh, Ir, Ni, Pd, Pt, Cu, Ag, Au, Zn, Cd, Hg, preferably Fe, Co, Ni, Cu, Ru, Pd, Pt, particularly preferably Cu, preferably on a customary support material, particularly preferably on a support material comprising the oxides of titanium, zirconium, hafnium, silicon and/or aluminum. Catalysts which can be used according to the invention can be produced by processes known from the prior art for producing such supported catalysts. Use can preferably also be made of supported catalysts comprising copper on a support material comprising aluminum oxide or titanium dioxide in the presence or absence of one or more of the elements magnesium, barium, zinc or chromium. Such catalysts and their production are known from WO 99/44974.

Furthermore, copper-comprising supported catalysts as described, for example, in WO 95/32171 and the catalysts disclosed in EP-A 44 444 and DE-A 1 957 591 are suitable for the hydrogenation according to the invention.

The hydrogenation can be carried out batchwise or continuously, e.g. in a reactor tube which is filled with a catalyst bed and in which the reaction solution is passed over the catalyst bed, e.g. in the downflow or upflow mode, as described in DE-A 19 41 633 or DE-A 20 40 501. It can be advantageous to recirculate a substream of the output from the reaction, if appropriate with cooling, and pass it over the fixed catalyst bed again. This recycle mode is preferably operated at a ratio of recycle to feed of 10-20:1. It can likewise be advantageous to carry out the hydrogenation in a plurality of reactors connected in series, for example in from 2 to 4 reactors, with the hydrogenation reaction being carried out only to a partial conversion of, for example, from 50 to 98% in the individual reactors upstream of the last reactor and the hydrogenation being completed only in the last reactor. It can be advantageous here to cool the hydrogenation output from the preceding reactor before it enters the next reactor, for example by means of cooling devices or by injection of cold gases such as hydrogen or nitrogen or by introduction of a substream of cold reaction solution.

The hydrogenation temperature is generally in the range from 50 to 180° C., preferably from 90 to 140° C. A hydrogenation pressure of generally from 10 to 250 bar, preferably from 20 to 120 bar, is employed.

The hydrogenation can be carried out with addition of an inert solvent. Solvents which can be used are water, cyclic ethers such as THF or dioxane and also acyclic ethers, likewise lower alcohols, e.g. methanol, ethanol or 2-ethylhexanol.

Otherwise, it is possible to employ any hydrogenation methods and hydrogenation catalysts which are customary for the hydrogenation of aldehydes and are described in detail in the standard literature.

EXAMPLES

Example 1

Hydrogenation of Hydroxypivalaldehyde to Neopentyl Glycol

Hydrogenation Feed 1.1 mol of isobuyraldehyde were stirred with 1 mol of formaldehyde in the form of a 40% strength solution and 4 mol % of trimethylamine, based on isobutyraldehyde, at 75° C. for 1 hour. The reaction solution was concentrated by distilling off low boilers such as isobutyraldehyde and part of the water at atmospheric pressure. The bottoms obtained comprised 75% by weight of hydroxypivalaldehyde, 20% by weight of water and about 5% by weight of other organic secondary components.

Production of the Catalyst

All percentages given under this subitem are, unless indicated otherwise, percentages by weight. The percentage compositions indicated are based on the oxidic constituents of the finished catalysts.

Starting materials were a 20% strength by weight sodium carbonate solution and an aqueous solution I comprising 2.67% by weight of Al and 5% by weight of Cu in the form of their nitrates.

In the precipitation, solution I and sodium carbonate solution were metered into a precipitation vessel at 80° C. in such a way that a pH of 5.6 was established. The precipitation mixture was transferred to a larger stirred vessel and was there brought to a pH of 7.9 at 80° C. by means of sodium carbonate solution. The suspension was then conveyed to a filter press.

The mixture was then filtered and washed with water until free of nitrate. The filter paste was suspended in water and dried in a spray drier by means of hot air at an outlet temperature of 130-150° C. A calcination was subsequently carried out at a temperature of 375-390° C. The powder was subsequently tabletted together with 3% by weight of graphite as auxiliary to give pellets having dimensions of 5×5 mm. The pellets obtained were then calcined at a temperature of 600° C. for 60 minutes in a heated rotary tube.

The catalyst produced in this way comprised 55% of CuO and 45% by weight of $Al_2O_3$, had a specific surface area (BET) of 95 $m^2/g$, an Hg porosity of 0.44 ml/g and a tapped density of 952 g/l.

205 g of this $Cu/Al_2O_3$ catalyst were activated by passing a mixture of 5% by volume of hydrogen and 95% by volume of nitrogen (total volume: 150 standard l/h) over the catalyst at 190° C. under atmospheric pressure for 24 hours in a tube reactor.

Hydrogenation

The mixture described above as hydrogenation feed served as starting solution. From 0 to 15% by weight (based on the hydrogenation feed) of a 15% strength by weight aqueous solution of trimethylamine were added to this mixture in order to set a pH of the hydrogenation output of greater than 8. The hydrogenation input obtained in this way was pumped over the catalyst at 37 bar and 105° C. in the downflow mode at a WHSV of 0.32 $kg_{HPA}/kg_{cat} \times h$ in a hydrogenation reactor having a liquid circuit (recycle:input=16:1) (hydrogen/hydroxypivalaldehyde molar ratio: about 1.5). A pH meter model 766 from Knick with a glass electrode N1041A from Schott was used for measuring the pH.

A mean conversion of 95.3% by weight at a mean pH of 8.8 was achieved over a number of days.

Comparative Example 1

Example 1 was repeated under the conditions indicated but 1% of CO was mixed into the hydrogen.

The mean conversion at this setting was 70.0% by weight at a mean pH of 8.2.

Example 2

Hydrogenation of Hydroxypivalaldehyde to Neopentyl Glycol

Hydrogenation Feed

The hydrogenation feed as described in example 1 was used.

Catalyst Used

The catalyst from example 1 was used.

Hydrogenation

The hydrogenation input was passed in the downflow mode at an $H_2$ pressure of 37 bar through the reactor which was heated to 105° C. The WHSV was 0.32 kg of HPA/ ($kg_{cat} \times h$). From 0 to 17% by weight (based on the hydrogenation feed) of a 50% strength by weight aqueous solution of trimethylamine were added to this mixture in order to set a pH of the hydrogenation output of greater than 8 (hydrogen/hydroxypivalaldehyde molar ratio: about 1.5). Part of the hydrogenation output was mixed back into the input (recycle mode). The ratio of recycle to input was 16:1. A mean conversion of 88.1% at a mean pH of 8.4 were achieved over a number of days.

Comparative Example 2

Example 2 was repeated under the conditions indicated but 10% of $CO_2$ was mixed into the hydrogen. Hydrogen/hydroxypivalaldehyde molar ratio: about 1.5.

To keep the $H_2$ partial pressure constant, the plant pressure was increased to 41 bar. The mean conversion at this setting was 75.3% at a mean pH of 8.0.

Example 3

Hydrogenation of Hydroxypivalaldehyde to Neopentyl Glycol

Hydrogenation Feed

The hydrogenation feed as described in example 1 was used.

Catalyst Used

The catalyst described in example 1 was used, but 3×3 mm pellets were produced.

The catalyst comprised 55% of CuO and 45% by weight of $Ak_2O_3$, had a specific surface area (BET) of 95 $m^2/g$, an Hg porosity of 0.38 ml/g and a tapped density of 1042 g/l.

Hydrogenation

The hydrogenation input was passed through the reactor in the downflow mode at an $H_2$ pressure of 40 bar. The temperature in the upper half of the reactor was 96° C., and that in the lower half was 106° C. The WHSV was 0.37 kg of HPA/($kg_{cat} \times h$). Together with the liquid input, about 110 mol % of $H_2$ (based on methyolalkanals used) were metered in, corresponding to a hydrogen/starting material molar ratio of 1:1. Part of the hydrogenation output was mixed back into the input (recycle mode). The ratio of recycle to input was 16:1. A mean conversion of 95.9% at a mean pH of 8.3 was achieved over a number of days.

Example 4

Example 3 was repeated under the conditions indicated but the amount of hydrogen was doubled to a hydrogen/ starting material molar ratio of 2.2 and the temperature was reduced to 93° C. in the upper half of the reactor and 103° C. in the lower half of the reactor. A mean conversion of 95.6% at a pH of 8.4 was achieved.

Example 5

Hydrogenation of Dimethylolbutanal (DMB) to TMP Hydrogenation Feed

The hydrogenation feed was prepared as described in example 6 of PCT/WO 98/28253.

Catalyst Activation 5.3 l of a Cu/TiO$_2$ catalyst B of PCT/WO 02/85825 were activated by passing a mixture of 2.5% by volume of hydrogen and 97.5% by volume of nitrogen (total volume: 600 standard l/h) over the catalyst at 190° C. under atmospheric pressure for 144 hours in a tube reactor.

Hydrogenation

The mixture described above as hydrogenation feed served as starting solution. The hydrogenation input was passed through the reactor in the downflow mode at 110° C. and an H$_2$ pressure of 90 bar. The WHSV was 0.2 kg of DMB/(I$_{cat.}$*h). Together with the liquid input, from 125 to 200 mol % of hydrogen (based on methyolalkanals) were fed in, corresponding to a hydrogen/methylolalkanal molar ratio of from 1.25 to 2.0. The plant pressure was kept constant at 90 bar (offgas mode). Part of the hydrogenation output was mixed back into the input (recycle mode). The ratio of recycle to feed was 6.5:1.

Table 1 shows the conversion over a period of 2112 hours and the amount of hydrogen metered in.

The analysis of the dimethylolbutanal content of the polyhydric alcohol obtained was carried out by means of gas chromatography (GC) on an HP5 column from J&W, injector: 280° C.; detection was effected by means of an FID (flame ionization detector).

TABLE 1

| Running time [h] | Hydrogen [mol % based on DMB] | DMB in the hydrogenation output [GC-% by area] |
|---|---|---|
| 0 | 125 | 0.25 |
| 216 | 125 | 0.37 |
| 624 | 125 | 0.86 |
| 816 | 125 | 1.24 |
| 864 | 200 | 1.10 |
| 1272 | 200 | 1.11 |
| 1440 | 200 | 1.38 |
| 1752 | 200 | 1.51 |
| 1800 | 125 | 1.95 |
| 1920 | 125 | 2.40 |
| 2112 | 125 | 2.80 |

It can clearly be seen that during the time periods during which only a small excess of hydrogen was used, a more rapid decrease in activity was observed than during periods with a large amount of offgas.

The invention claimed is:

1. A process for preparing a polyhydric alcohol comprising catalytic hydrogenation of a methylolalkanal according to the following general formula:

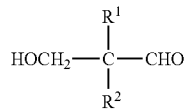

wherein $R^1$ and $R^2$ each independently represent a methylol group, a $C_1$-$C_{22}$ alkyl group, a $C_6$-$C_{33}$ aryl group, or a $C_6$-$C_{33}$ aralkyl group, in a liquid phase with hydrogen over a hydrogenation catalyst, wherein a molar ratio of hydrogen to methylolalkanal is greater than 1.

2. The process according to claim 1, wherein the molar ratio of hydrogen to methylolalkanal is from 5 to 1.

3. The process according to claim 1, wherein the molar ratio of hydrogen to methylolalkanal is from 2.5 to 1.1.

4. The process according to claim 1, wherein a hydrogenation feed comprises methylolalkanal and less than 5 wt. % formaldehyde.

5. The process according to claim 1, further comprising adding at least one tertiary amine, inorganic base, inorganic acid, or organic acid to a hydrogenation feed comprising methylolalkanal to obtain a hydrogenation output having a pH of from 7.0 to 9.0.

6. The process according to claim 5, wherein at least one tri-n-alkylamine is added to the hydrogenation feed.

7. The process according to claim 5, wherein at least one of trimethylamine, triethylamine, tri-n-propylamine, and tri-n-butylamine is added to the hydrogenation feed.

8. The process according to claim 5, wherein at least acetic acid is added to the hydrogenation feed.

9. The process according to claim 5, wherein the pH is from 8.0 to 9.0.

10. The process according to claim 1, wherein the hydrogenation catalyst comprises at least one metal of transition groups 8 to 12 of the Period Table of the Elements.

11. The process according to claim 10, wherein the hydrogenation catalyst comprises at least one metal selected from Fe, Ru, Co, Ni, Pd, Pt, and Cu.

12. The process according to claim 10, wherein the hydrogenation catalyst is a supported catalyst.

13. The process according to claim 10, wherein the hydrogenation catalyst is a supported catalyst comprising an oxide of titanium, zirconium, hafnium, silicon and/or aluminum as a support material.

14. The process according to claim 10, wherein the hydrogenation catalyst is a supported catalyst comprising copper on a titanium dioxide support material in the presence or absence of one or more of magnesium, barium, zinc and chromium.

15. The process according to claim 10, wherein the hydrogenation catalyst is a supported catalyst comprising copper on an aluminum oxide support material in the presence or absence of one or more of magnesium, barium, zinc and chromium.

16. The process according to claim 1, wherein the methylolalkanal is hydroxypivalaldehyde.

17. The process according to claim 1, wherein the methylolalkanal is pentaerythrose.

18. The process according to claim 1, wherein the methylolalkanal is dimethylolbutanal.

* * * * *